United States Patent [19]
Munder et al.

[11] 3,941,662
[45] Mar. 2, 1976

[54] APPARATUS FOR CULTURING CELLS

[75] Inventors: Paul Gerhard Munder, Emmendingen; Manuel Modolell, Bollschweil, both of Germany; Donald Francis Hoelzl Wallach, Boston, Mass.

[73] Assignee: Max-Planck-Gesellschaft zur Forderung der Wissenschaften e.V., Goettingen, Germany

[22] Filed: Mar. 21, 1975

[21] Appl. No.: 560,632

Related U.S. Application Data

[62] Division of Ser. No. 260,629, June 7, 1972, Pat. No. 3,873,423.

[30] Foreign Application Priority Data

June 9, 1971  Germany............................ 2128744

[52] U.S. Cl. ............... 195/127; 195/142; 195/109; 195/118
[51] Int. Cl.² .......................................... C12B 1/00
[58] Field of Search ............ 195/127, 142, 109, 118

[56] References Cited
UNITED STATES PATENTS

| | | |
|---|---|---|
| 3,407,120 | 10/1968 | Weiss et al.......................... 195/142 |
| 3,821,087 | 6/1974 | Knazek et al...................... 195/127 |

*Primary Examiner*—Alvin E. Tanenholtz
*Attorney, Agent, or Firm*—Hans Berman

[57] ABSTRACT

Cells are grown in a layer attached to the roughened inner wall of a container of fluorinated ethylenepropylene copolymer filled with a culture medium buffered with bicarbonate ions. The pH of the medium is monitored and maintained by varying the rate at which carbon dioxide is fed to the gas phase in an incubator enclosing the container which is permeable to gas, but impermeable to liquid. The partial pressure of oxygen in the gas phase is monitored, and controlled by varying the rate at which oxygen is fed to the incubator. Nitrogen is fed to the incubator at a rate varying inversely to the change in carbon dioxide feeding rate to maintain the partial pressure of oxygen under otherwise stable conditions. The medium may be pumped through the container intermittently or continuously and may be replaced by fresh medium when pH changes cannot be compensated by varying the carbon dioxide feeding rate.

8 Claims, 3 Drawing Figures

APPARATUS FOR CULTURING CELLS

This is a division of application Ser. No 260,629, filed June 7, 1972, now U.S. Pat. No. 3,873,423.

This invention relates to the culturing of cells, and particularly to the culturing of cells of animal origin. In its more specific aspect, the invention is concerned with a method of culturing cells suitable for cell production on a relatively large scale, and to apparatus for performing the method.

Cells are commonly cultured in vitro over extended periods of time for screening chemical compounds for their physiological effects prior to testing on laboratory animals and ultimately on humans However, the culturing methods in present use cannot approach conditions prevailing in a living body closely enough for providing more than an approximate correlation. The results obtained in cell cultures cannot be duplicated in test animals in many instances. There is a well recognized need for cell culturing methods which permit a more reliable prediction of the behaviour of cells in a living creature.

The partial pressures of carbon dioxide and oxygen in the environment of cells of living beings are known to be maintained at normally constant values by physiological feedback mechanisms. Yet, such partial pressures cannot be controlled by methods available heretofore in cell layers cultured outside the animal body. In some instances, the pH value of the culture medium is monitored and may be adjusted and maintained by electronic feedback mechanisms. The known devices for maintaining pH in a culture medium, however, are complex, and are not commonly employed for this reason outside of the fermentation industry.

The effects of carbon dioxide pressure on a cell culture are not yet precisely known. It has been suggested that carbon dioxide causes the formation of protein carbamates. The effects of oxygen pressure are better understood. Partial oxygen pressures greater than those in atmospheric air are known in many instances to enhance the growth of tumors, and to cause death of cells and of the entire animal even in the absence of tumors.

It is a primary object of this invention to provide a method of culturing cells under controlled conditions of oxygen and carbon dioxide pressure. A concomitant object is the provision of apparatus for performing the method.

With these and other objects in view, the invention in one of its more specific aspects provides a method in which a container of a material permeable to gases, but impermeable to liquid, is charged with a liquid culture medium containing bicarbonate ions and capable of sustaining growth of the cells to be cultured. The container is also charged with an inoculum of such cells and placed in an incubator enclosure. The partial oxygen pressure in the enclosure and the pH value of the medium are sensed, and carbon dioxide and oxygen are fed to the incubator enclosure at a rate to maintain the pH value in the medium and the partial oxygen pressure in the enclosure substantially constant.

The apparatus employed includes a substantially gastight incubator enclosure and a plurality of containers supported in the enclosure. Each container essentially consists of chemically inert material premeable to gas, but impermeable to liquid. A pump may be provided for circulating a stream of liquid culture medium through the containers. A first detecting device senses the pH value of the medium, and a second detecting device senses the partial pressure of oxygen in the enclosure and outside the container. Valves are interposed between the enclosure and respective sources of carbon dioxide and oxygen under pressure and are operatively connected to the detecting devices for admitting carbon dioxide and oxygen to the enclosure at rates responsive to the sensed pH value and the sensed oxygen pressure respectively.

Other features, additional objects, and many of the attendant advantages of this invention will readily become apparent from the following detailed description of preferred embodiments when considered in connection with the appended drawing in which.

Figure 1:
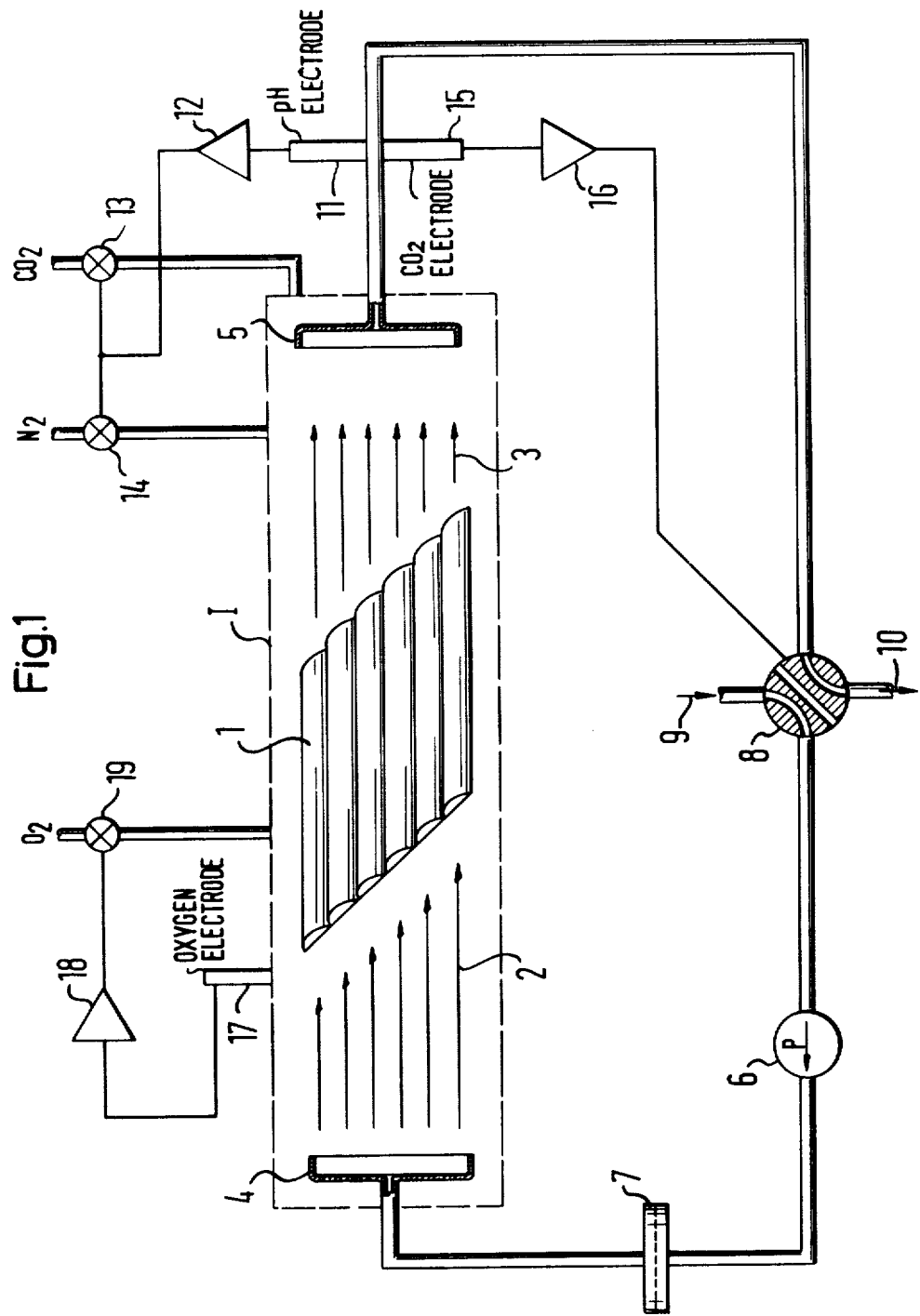
FIG. 1 shows apparatus of the invention partly in elevational section and partly by conventional symbols.

Referring now to the drawing in detail, and initially to FIG. 1, a broken line I indicates a gastight incubator, the interior of which is held at a precisely controlled, uniform temperature by electric heating elements and thermostats, not shown and conventional in themselves. Integrally connected, tubular containers 1 are supported in the incubator I in a common plane. They essentially consist of two sheets of fluorinated ethylenepropylene copolymer (Teflon FEP) heat-sealed along spacedly parallel seams. Feed pipes 2 are sealed to the longitudinal ends of respective containers 1 which are at the left in FIG 1, and discharge pipes 3 are similarly sealed to the right ends. Except for openings communicating with the pipes 2, 3, the containers 1 are sealed and impermeable to liquids, but the sheet material is only 25 $\mu$m thick and permeable to gases.

The pipes 2, 3 are connected to respective feed and discharge manifolds 4, 5 connected by a circulating system including a pump 6, a ceramic filter 7, and a rotary control valve 8. In the illustrated position of the valve, an aqueous culture medium is drawn by the pump from a storage container (not shown), as indicated by the arrow 9, and discharged to another storage container or to waste after passing through the containers 1 as indicated by an arrow 10, but not otherwise illustrated. When the valve 8 is shifted clockwise 45°, as will presently be described, the same liquid is circulated through the containers 1 as long as the pump 6 operates.

The hydrogen ion concentration in the liquid leaving the discharge manifold 5 is monitored by a pH-responsive glass electrode 11 in conventional, non-illustrated cooperation with a Ag/AgCl reference electrode The output signal of the electrode, amplified by an amplifier 12, is fed to electrically operated control valves 13, 14. The valve 13 connects the interior of the incubator I with a storage tank for carbon dioxide under pressure, and the valve 14 similarly connects the incubator to a nitrogen tank. As is not explicitly shown in the drawing, the gases pass through water-filled gas washing bottles so that they re saturated with water vapor at the temperature of the incubator I.

The partial pressure of carbon dioxide in the incubator is separately sensed in the circulating liquid by a $CO_2$-electrode 15. The output of the electrode 15 is amplified by the amplifier 16 to control the solenoid, not shown, which may shift the valve 8 into the illustrated position against the restraining force of a return spring. The oxygen concentration in the gas phase of the incubator is monitored by an oxygen electrode 17. The output signal of the electrode 17, amplified by an amplifier 18, operates a control valve 19 which admits moist oxygen from a tank to the incubator 1.

The inner face of the containers 1 are chemically etched prior to heat sealing to make them sufficiently hydrophilic and to improve adhesion of cells that it is desired to cultture. The cells or tissue may be introduced into the containers 1 under sterile conditions together with a necessary amount of culture medium through one of the terminal openings before connecting the opening to an associated tube 2, 3, or a cell suspension may be injected through the wall of the container into the liquid medium by means of a syringe carrying a fine needle. The puncture is sealed spontaneously by the resilient sheet material upon withdrawal of the needle. If the pump 6 is reversed, and the valve 8 is turned manually 90° from the illustrated position, the cells or tissue may also be introduced into the system as a suspension in the culture medium introduced as indicated by the arrow 9. The pump 6 is deenergized for one hour or longer after the cells are introduced into the containers 1 so as to permit the cells to attach themselves to the rough container wall. They are anchored to the wall with sufficient strength to withstand later circulation of the liquid medium.

The medium is buffered by bicarbonate ions, and the composition of the medium changes as the cells grow and multiply. As soon as the cells cling firmly to the container wall, the pump 6 is operated continuously or intermittently to permit the values of pH, $CO_2$, and oxygen to be tested by the electrodes 11, 15, 17 and adjusted before they greatly deviate from the desired values.

The cells and the gas phase in the enclosure of the incubator 1 are in direct gas equilibrium through the permeable walls of the containers 1. While cells are being grown in the containers, the inculator 1 is held at a desired temperature, typically 37°C, and the pH of the circulating medium, the partial pressure of $CO_2$ in the gas phase, and the bicarbonate ion concentration in the medium then satisfy the Henderson-Hasselbach equation:

$$pH_{37°} = 6.06 + \log \frac{[HCO_3^-]}{0.024 \cdot pCO_2}$$

The bicarbonate ion concentration may conveniently be chosen at 0.024 mole, and the pH chosen may be 7.1 ± 0.05. The amplifier 12 is thus set to open the valve 13 wider when the pH sensed by the electrode 11 rises to 7.15, and to throttle flow through the valve 13 when the pH is lowered by the admitted carbon dioxide to 7.05. The nitrogen valve 14 admits a continuous stream of nitrogen and throttles the nitrogen supply when the valve 13 is opened, while increasing the nitrogen stream when the valve 13 is moved toward the closing position, the valves 13, 14 being balanced in such a manner as to maintain a steady partial pressure of oxygen in the incubator 1 under otherwise stable conditions.

The oxygen concentration is kept at a desired value, that may be set on the amplifier 18, by the valve 19 in response to the output signal of the electrode 17, oxygen entering the incubator in a normally continuous stream. A non-illustrated pressure relief valve maintains a desired total gas pressure in the incubator.

Lactid acid is produced by many growing cells and accumulates in the circulating liquid to such an extent that the desired pH may no longer be maintained by reducing the $CO_2$ supply. When the concentration of buffering $HCO_3$ ions drops below a value that may be chosen by setting the amplifier 16, the amplified output signal of the electrode 15 shifts the valve 8 into the illustrated position. At least a portion of the circulating culture medium is thereby replaced by fresh medium uncontaminated by the products of cell metabolism.

The apparatus shown in FIG. 1 permits culturing of cells in a much smaller incubator enclosure than would be required for culturing cells at a comparable rate by conventional methods. Even less space is occupied by the apparatus illustrated in FIGS. 2 and 3 only to the extent required for an understanding of the invention.

A turntable 20 is mounted on the upright output shaft 21 of a gear motor 22 equipped with an internal, non-illustrated clutch which turns the shaft 21 through a small acute angle, thereafter stops the shaft for a fixed period, such as about 1 minute, whereupon the cycle is repeated. The turntable carries circumferentially juxtaposed, wedge-shaped incubator enclosures 23 kept at a desired temperature by electric heating elements (not shown) which may be embedded in the turntable 20. The apex angle of each enclosure 23 corresponds to the angular movement of the shaft 21 during each cycle.

An end plate 24 at the radially outer end of each enclosure 23 is removable to provide access to the enclosure, and has a radial passage 25 aligned with a corresponding passage 26 in the raised outer rim of the turntable. A check valve is provided in the passage 25 to permit outward flow of gas from the container 23, but to prevent inward flow. The valve is not capable of pictorial representation on the scale of FIGS. 2 and 3, and is conventional in itself.

The opposite narrow end plate 27 of each enclosure is provided with a radial passage 28 and with a non-illustrated valve in the passage which may be opened by an inserted hollow needle 29 defining a control station, but is normally closed. The needle 29 is mounted on the armature of a solenoid 30 fastened to the shell of the motor 22. A flexible hose 31 connects the needle 29 to valves 32, 33, 34. The valves are connected to respective, non-illustrated tanks containing nitrogen, carbon dioxide, and oxygen under pressure.

Two wide-meshed, stainless steel screens 35, 36 are retained in each enclosure 23 in parallel relationship between bosses 37 and support therebetween individual containers 38 of Teflon FEP similar to those described with reference to FIG. 1. The containers 38 are sealed tubes flattened between the screens 35, 36.

Near the radially outer end of each enclosure 23, its top and bottom walls are provided with vertically aligned quartz windows 39 aligned with corresponding apertures 40 in the turntable 20. The beam 41 of a light source, not itself shown, passes through a filter 42 which transmits only a narrow range of wave lengths. The filtered beam is reflected by a mirror 43 through a condensing lens 44 on the aligned windows 39 of the enclosure 23 temporarily halted at the control station.

The light released from the top wall of the enclosure 23 passes through a quartz diffuser 45 and is directed by a lens 46 on a photoelectric cell 47. The output of the cell is amplified by an amplifier 48 to operate the afore-mentioned valves 32, 33, one being moved toward the closed position while the other moves toward the open position, as described with reference to valves 13, 14 in FIG. 1. The oxygen valve 34 is controlled by an oxygen electrode, not shown, and inserted into the container 23 together with the needle 29. The valves admit gases to the container 23 as long as it is halted at the control station and the needle 29 is inserted. The solenoid is energized as long as the shaft 21 stands still so that gas flows to each container 23 for a uniform period at a rate set by the valves 32, 33, 34.

Figure 2:
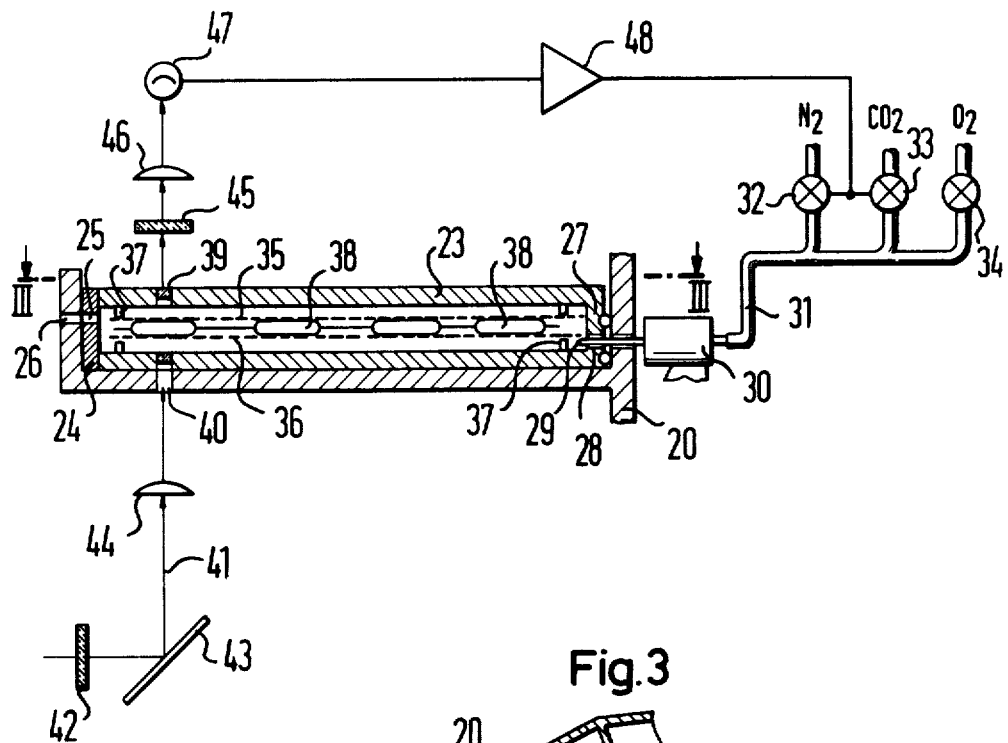
FIG. 2 illustrates additional apparatus of the invention in fragmentary elevational section on the line II — II of FIG. 3.
Figure 3:
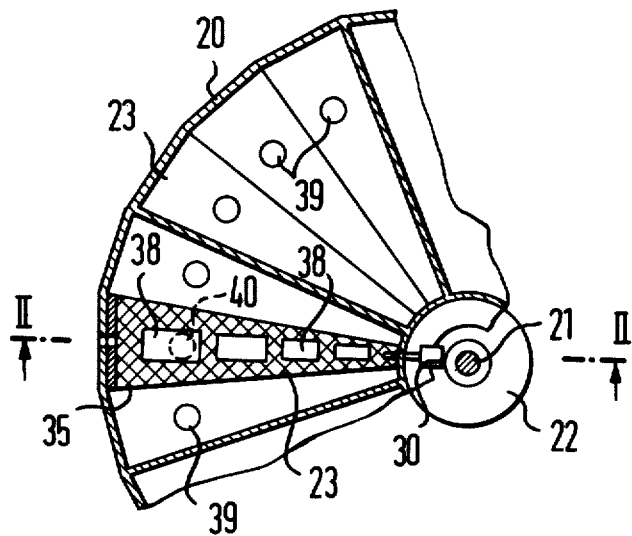
FIG. 3 is a fragmentary top plan view of the device of FIG. 2 on a smaller scale, portions of the structure being broken away to reveal normally concealed features.

In operating the apparatus shown in FIGS. 2 and 3, the sealed containers 38 are sterilized by exposure to ultraviolet light, and a suspension of cells to be cultured in a suitable culture medium containing bicarbonate ions and an indicator having a pK value in the desired range of about 7.0 to 7.4, such as bromethymol blue or cresol red, is injected into each container 38 intended for the same enclosure 23. While all containers on the turntable 20 may contain inocula of the same type of cells, different cultures may be produced simultaneously in different enclosures.

The containers 38 intended for the same enclosure 23 are placed between the screens 35, 36 and slipped into the enclosure through the open wide end of the same in such a manner that one of the containers is located in the path of the beam 41. The thickness of the culture medium intercepting the beam is precisely determined by the bosses 37 and the thicknesses of the screens 35, 36 and of the sheet material constituting the container 38. When the filter 42 is properly chosen for the color change of the indicator employed, the output of the cell 47 is indicative of the pH of the culture medium for operating the valves 32, 33 in a manner evident from the mode of operation of the first-described embodiment.

Exhaustion of the buffering bicarbonate in the culture medium may be indicated by a carbon dioxide electrode (not shown) introduced into the gas space of the enclosure 23 with the needle 29, or a signal may be provided by the cell 47 calling for an operator to replace the medium in the containers 38.

The devices shown in the drawing have been used successfully for growing cells under precisely controlled conditions of partial oxygen and carbon dioxide pressures, and precisely controlled pH, and for evaluating the effects of variations in these parameters and in the composition of the culture medium, as by addition of chemicals to be tested for their physiological action.

The output of the photoelectric cell 47 is indicative of the density of the culture in the container 38 when the filter 42 is replaced by one permeable only to light having a wavelength outside the color range of the indicator employed, for example 256 m$\mu$, and the windows 39 permit direct microscopic examination of the cells in the aligned container. The influence of varied culturing conditions may thus be observed readily.

Obviously, the invention is not limited to specific cells nor to the culture medium capable of sustaining their growth, as long as the latter contains a bicarbonate buffer system. Many types of cells have been cultured successfully in apparatus of the invention under controlled partial pressures of oxygen and carbon dioxide.

Such cells include mouse peritoneal cells which were cultured in Eagle's medium + 20% fetal calf serum at pH 7.1; cells of the same type cultured in Eagle's medium + 20% inactivated 0 Rh+ human serum, pH 7.1; primary rat fibroblasts cultured in Eagle's medium + 20% inactivated calf serum, pH 7.3; and bovine mammary tissue culture in Eagle's medium + 20% fetal calf serum, pH 7.2.

The cultures mentioned above were held under a total gas pressure not significantly different from ambient gas pressure by suitable choice of the pressure relief valves on the incubator enclosures I, 23, but total gas pressures significantly higher and lower can be resorted to in an obvious manner if so desired. When operating at room pressure, a partial oxygen pressure of approximately 135 mm Hg may be chosen as a starting condition and may be modified as conditions warrant, while a carbon dioxide pressure of 100 mm Hg is calculated from the Henderson-Hasselbach equation under the conditions indicated above which may be considered typical. Nitrogen and water vapor saturating the gases at the practically constant temperature of the incubator enclosure account for the balance of the total gas pressure.

Inasmuch as the partial pressure of carbon dioxide and oxygen, the total gas pressure, the temperature, the pH value, and the basic composition of the culture medium may be among the variables to be investigated in conjunction with the physiological effect of tested chemicals, the exemplary date given above will be understood merely to provide starting conditions for investigations which may lead to very different operating parameters readily maintained by the disclosed apparatus.

Fluorinated ethylene-propylene copolymer in a thickness of 10 to 100 $\mu$m has been found to be the best material available to us at this time for making the containers 1, 38. It is chemically fully inert under the conditions of the instant invention and transparent both to visible light and to ultraviolet light, thereby permitting convenient sterilization by exposure to ultraviolet light for 10 to 15 minutes and the opitcal pH determination illustrated in FIGS. 2 and 3. Its surface can be made adequately hydrophilic by simple chemical etching to permit the cells to attach themselves to the container wall. The material also is readily welded or heat-sealed by the type of equipment commonly employed for thermoplastics.

Other fluoroplastics, such as polytetrafluoroethylene and copolymers of hexafluoropropylene and tetrafluoroethylene combine fewer of the desirable properties indicated above, but may also be resorted to.

The shape of the containers which are charged with the culture medium and an inoculum of the cells to be cultured is not critical. Depending on the incubator enclosure employed and the arrangment of the containers in the enclosure, the containers may have a width and length between 1 and 200 cm, and a height of 0.5 to 50 mm, these dimensions, however, being capable of further modification, if so desired, and not critical.

Although the cells attach themselves to the container wall with sufficient strength to permit pumping of the culture medium through the container, as is shown in FIG. 1, the culture is readily harvested by releasing the cells from the walls after treatment with trypsin or other enzymes or chemicals as is known in this art. The cells adhere to the plastic wall much less tenaciously than to glass, and it is frequently possible to peel a coherent layer of cells, particularly a monolayer, from the container wall after repeatedly folding and otherwise deforming the latter.

It is an outstanding feature of this invention that the inoculated medium is sealed from contamination by solids or liquids through the entire culturing period in a simple and effective manner. The circulating system illustrated in FIG. 1 preferably employs a peristaltic pump whose tube may be connected directly to the valve 8 and the filter 7.

While the invention has been described particularly with reference to the culturing of cells of animal origin in a manner suitable for testing the physiological effects of chemicals added to the culture medium, it will be appreciated that products of cell metabolism may be recovered from the culture medium and provide the principal incentive for performing the method of the invention.

It should be understood, therefore, that the foregoing disclosure relates onto to preferred embodiments of the invention, and that it is intended to cover all changes and modifications of the examples of the invention herein chosen for the purpose of the disclosure which do not constitute departures from the spirit and scope of the invention set forth in the appended claims.

What is claimed is:

1. Apparatus for culturing cells comprising, in combination:
    a. a substantially gas-tight incubator enclosure;
    b. support means in said enclosure;
    c. a plurality of containers on said support means,
        1. each container essentially consisting of chemically inert material permeable to gas, but impermeable to liquid;
    d. pump means for circulating a stream of liquid culture medium through said containers;
    e. first detecing means for sensing the pH value of the circulating culture medium;
    f. second detecting means for sensing the partial pressure of oxygen in said enclosure outside said containers;
    g. a source of carbon dioxide under pressure;
    h. a source of oxygen under pressure;
    i. first valve means interposed between said source of carbon dioxide and said enclosure and operatively connected to said first detecting means for admitting said carbon dioxide to said enclosure in response to the sensed pH value;
    j. second valve means interposed between said source of oxygen and said enclosure and operatively connected to said second detecting means for admitting said oxygen to said enclosure in response to the sensed partial pressure; and
    k. means for maintaining a substantially constant total gas pressure in said enclosure.

2. Apparatus as set forth in claim 1, wherein said material is a sheet material permeable to light, said sheet material having an inner face in said container and an outer face exposed in said enclosure, said inner face being rougher than said outer face.

3. Apparatus as set forth in claim 2, wherein said sheet material essentially consists of a fluoroplastic.

4. Apparatus as set forth in claim 3, wherein said fluoroplastic is a copolymer of fluorinated ethylene and propylene.

5. Apparatus as set forth in claim 2, wherein the thickness of said sheet material is between 10 and 100 $\mu$m.

6. Apparatus as set forth in claim 1, further comprising a source of nitrogen under pressure, and third valve means interposed between said source of nitrogen and said enclosure and operatively connected to said first detecting means for admitting said nitrogen to said enclosure in response to the sensed pH value, the rate of nitrogen admission being varied inversely to the variation in the rate of carbon dioxide admission.

7. Apparatus for culturing cells comprising, in combination:
    a. a carrier;
    b. a plurality of gas-tight incubator enclosures on said carrier;
    c. drive means for moving said carrier and for thereby moving said enclosures sequentially and cyclically through a control station;
    d. support means in each enclosure;
    e. a container on said support means, said container essentially consisting of chemically inert material permeable to gas, but impermeable to liquid;
    f. first detecting means at said control station for sensing the pH value of a liquid in said container;
    g. second detecting means for sensing the partial pressure of oxygen in each enclosure;
    h. a source of carbon dioxide under pressure;
    j. a source of oxygen under pressure;
    k. first valve means connected to said source of carbon dioxide and to said first detecting means for admitting carbon dioxide to each enclosure in response to the sensed pH value while the enclosure is at said control station; and
    l. second valve means connected to said source of oxygen and to said second detecting means for admitting oxygen to each enclosure in response to the sensed partial pressure thereof while the enclosure is at said control station.

8. Apparatus as set forth in claim 7, wherein each enclosure has two wall portions permeable to light, said container being permeable to light and located between said two wall portions, said first detecting means including a source of a beam of light directed against one of said wall portions when said enclosure is in said control station for passage of said beam through said container, and a photoelectric cell located for receiving the portion of said beam released through the other wall portion.

* * * * *